United States Patent
Doci

(10) Patent No.: US 9,381,081 B2
(45) Date of Patent: Jul. 5, 2016

(54) INTRAOCULAR LENS HAVING HELICAL HAPTICS OF SHAPE MEMORY

(75) Inventor: Violeta Doci, Sierksdorf (DE)

(73) Assignee: Doci Innovations GmbH (Claus Simandi), Sierksdorf (DE)

( * ) Notice: Subject to any disclaimer, the term of this patent is extended or adjusted under 35 U.S.C. 154(b) by 120 days.

(21) Appl. No.: 14/384,492

(22) PCT Filed: Mar. 12, 2012

(86) PCT No.: PCT/IB2012/000488
§ 371 (c)(1),
(2), (4) Date: Dec. 8, 2014

(87) PCT Pub. No.: WO2013/136105
PCT Pub. Date: Sep. 19, 2013

(65) Prior Publication Data
US 2015/0127101 A1    May 7, 2015

(51) Int. Cl.
*A61F 2/16* (2006.01)
*A61L 27/06* (2006.01)
*A61L 27/30* (2006.01)
*A61L 27/04* (2006.01)

(52) U.S. Cl.
CPC .............. *A61F 2/1635* (2013.01); *A61F 2/1629* (2013.01); *A61L 27/047* (2013.01); *A61L 27/06* (2013.01); *A61L 27/306* (2013.01); *A61F 2002/1683* (2013.01); *A61F 2210/0014* (2013.01); *A61L 2400/16* (2013.01); *A61L 2430/16* (2013.01)

(58) Field of Classification Search
CPC ....................... A61F 2/1629; A61F 2002/1683
USPC ............ 623/6.37, 6.39, 6.42, 6.51, 6.53, 6.54
See application file for complete search history.

(56) References Cited

U.S. PATENT DOCUMENTS

| | | | |
|---|---|---|---|
| 4,615,701 A | 10/1986 | Woods | |
| 4,666,445 A * | 5/1987 | Tillay | A61F 2/1613 623/6.18 |
| 4,871,362 A * | 10/1989 | Nurmamedov | A61F 2/1613 623/6.58 |
| 6,096,078 A | 8/2000 | McDonald | |
| 6,443,984 B1 | 9/2002 | Jahn et al. | |

(Continued)

FOREIGN PATENT DOCUMENTS

| | | | |
|---|---|---|---|
| DE | 3722732 A1 | 1/1989 | |
| DE | 10062218 A1 | 7/2001 | |

(Continued)

OTHER PUBLICATIONS

International Search Report for PCT/IB2012/000488 mailed Nov. 13, 2012.

*Primary Examiner* — David H Willse
*Assistant Examiner* — Javier Blanco
(74) *Attorney, Agent, or Firm* — Drinker Biddle & Reath LLP

(57) ABSTRACT

For easy handling at placement of intra ocular lenses (IOLs) for cataract operations, these are equipped with helical haptics of memory materials circumferring the lens. Said haptics adhere to the rim of the lens as long as being cooled down to constriction temperature. On regaining body temperature the haptics expand and fit into the ridges of the eye's capsule sack. Accommodation then is achieved with constriction of the capsule sack by pressure transfer to the rim of the lens to form its shape, in multiplying it with some protrusion towards the pupil.

6 Claims, 2 Drawing Sheets

(56) References Cited

U.S. PATENT DOCUMENTS

| | | |
|---|---|---|
| 6,638,304 B2 | 10/2003 | Azar |
| 6,986,787 B1 * | 1/2006 | Baker, Jr. .............. A61F 2/1629 623/6.37 |
| 8,043,370 B2 | 10/2011 | Bretthauer et al. |
| 2002/0095212 A1 | 7/2002 | Boehm |
| 2002/0138140 A1 | 9/2002 | Hanna |
| 2003/0149480 A1 | 8/2003 | Shadduck |
| 2004/0111152 A1 | 6/2004 | Kelman |
| 2004/0181279 A1 | 9/2004 | Nun |
| 2004/0215340 A1 | 10/2004 | Messner et al. |
| 2006/0136055 A1 | 6/2006 | Michel |

FOREIGN PATENT DOCUMENTS

| | | | |
|---|---|---|---|
| DE | 20111320 U1 | 10/2001 | |
| DE | 9422429 U1 | 1/2002 | |
| DE | 10125829 A1 | 11/2002 | |
| DE | 10139027 A1 | 2/2003 | |
| EP | 0246216 A2 | 11/1987 | |
| FR | 2666504 A1 * | 3/1992 | ............ A61F 2/1613 |
| WO | WO 9215260 A1 * | 9/1992 | ............... A61F 2/16 |
| WO | WO-9506446 A2 | 3/1995 | |
| WO | WO-02083033 A2 | 10/2002 | |
| WO | WO-03017873 A1 | 3/2003 | |
| WO | WO-2004004605 A1 | 1/2004 | |

\* cited by examiner

INTRAOCULAR LENS HAVING HELICAL HAPTICS OF SHAPE MEMORY

CROSS-REFERANCE TO RELATED APPLICATIONS

This application is a national stage application (under 35 U.S.C. §371) of PCT/IB2012/000488, filed Mar. 12, 2012, which is incorporated herein by reference in its entirety.

FIELD OF THE INVENTION

The invention relates to an implantable artificial lens system for replacement in cataract surgery, having accomodative qualities.

Problem to be Solved

The accommodative capacity of the human eye is lost when the opaque human lens is replaced by a 20 rigid artificial lens in a cataract operation. A number of implantable artificial lens systems with variable focal length have been developed in view of presbyopia and cataract operation.

The potentially accommodative intraocular lenses are lenses or lens systems that are inserted into 25 the eye to replace the natural lens after it is removed by surgery, and which are mostly fixed in the capsular sack.

Under the influence of a still present but possibly weakened residual contraction of the ciliary muscle, axial displacement or more spherical deformation of the lens is aimed at through pressure transfer by haptics that are fixed to the IOL rims.

This so far had been only partly feasible in IOL surgery, due to the fact that strong haptics can hardly be inserted through the sklera (and pupil) into a delicate capsule sack—which both must carefully be cut to open a small gap, for not to damage it. Soft haptics in return are not capable of transmitting all pressure which would be required to deform 35 or displace the lens adequately, due to internal deformation. Moreover, hitherto it is not possible to find a method to regularly position the IOL system to the optimum site in the back of the capsule sack, without having to rely on outstanding skills of the operator, or without making bigger cutouts in the cornea or the front part of the capsule sack.

For to insert the artificial lens through small openings, it is a common technique to fold and inject it trough a thin cannulae.

When deploying it into the capsule sack it must be unfurling due to its own elasticity and its haptics should align in a way, that they snap into the ridges of the capsule sack or—in case of its decay—into the crease of the ciliaric muscle, for to transfer its contraction to the rim of the lens.

However, multiple attempts to implement this had not been too successful: Either the haptics were designed too big and too stiff for injecting it through a cannulae, or they did not provide sufficient pressure transfer to effectuate an adequate focusing.

Another problem of IOL surgery is, that quite a few patients suffer from post-operational ailments, as irregular definition and dazzling, as well as of effects resulting from astigmatism.

Common reason for this is, that artificial lenses are mostly offered with diametrically positioned haptics. Aside from sometimes deficient positioning, astigmatism here mainly results from irregular deformation of the lens due to unbalanced pressure on its rim, if the haptics are fixed only at a few points on the rim and are straightly outwards orientated—which is as more detrimental to sight, the stiffer the haptics are.

Moreover, another problem has to be solved: the position of the lens within the capsule sack in conventional systems is not always stable after operation, so that accelerations of the head, particularly in sports or with accidents, can cause lasting defocussing.

Task of This Invention

It is therefore subject of the here disclosed invention to design a lens system, the haptics of which would be foldable to a wide extent, but capable of transmitting the contractional forces from the ridge of the capsule sack or from the sulcus of the ciliary muscle to accommodate the lens to clear sight from close to far.

It therefore is the task of the here disclosed invention, to solve the problem of these contradictional demands: effective transfer of the ciliar muscle force and small shape of the implant, particularly 30 without haptics, which would obstruct the operation.

Furthermore the haptics should be designed so that they fit the lens exactly into place and let it effectively accommodate without irregular deformation, even if some fibrosis has hardened the capsule sack.

Prior Art

US Patent Application No. 2004/0,181,279 A1 describes a deformable lens that does not require the capsular sack to be deformable. In this case, the axial force operating through the movement of the ciliary muscle between the capsular sack that is rigid but can still be moved by the zonular fibres, and a firmly fixed plate placed outside the capsular sack is supposed to press a transparent deformable body into an orifice in this plate in such a way that the radii of curvature of the transparent deformable body are changed inside this orifice. However, an increased vertex power would only be expected in the case of a relaxed ciliary muscle if the zonular fibres tensed the capsular sack. A physiological adaptation, i.e. a learning process to tense the ciliary muscle for near vision would therefore be needed here. New designs that eliminate this problem have been promised in the literature.

U.S. Pat. No. 6,096,078 describes an intraocular lens that is implanted into the ciliary sulcus to supplement a conventional intraocular lens, and which is supposed to be axially displaceable by the movement of the ciliary muscle. It also has sensors to detect information (data) about the physical state of the lens, especially the mechanical tension in the haptic. This information is transmitted to an external evaluating unit via an electrical connection located on the circumference of the lens or on the haptics. The subject of this U.S. Pat. No. 6,096,078 does not include the concept of a closed control circuit but merely offers the possibility of detecting the activity of the ciliary muscle.

U.S. Pat. No. 6,638,304 describes an intraocular lens which is made of an electro-optical material (liquid crystals), is fitted with electrode structures, and alters the imaging behavior of the optical system. The information is obtained either by measuring the distance from the object of fixation (autonomic autofocus) or by using biological signals, which includes the following: registration of the signals that control the accommodation, namely the perception of the mechanical action of the ciliary muscle via a pressure sensor, the detection of the electrical activity of the ciliary muscle by surface electrodes, the detection of the tension in the zonular fibres, and the detection of the deformation of the capsular sack. The inventors suggest that the control signals of the iris contraction can be registered. They also mention the registration of the control signals of vergence, for which the contraction of a single external eye muscle (musculus rectus) is supposed to be detected mechanically, or else its neuronal innervation is to be detected electrically. A closed control circuit is achieved with the aid of a microcontroller. The power can be supplied by a battery or a photocell.

An accommodative intraocular lens for implantation in the human eye is described for example in German Patent No. 94 22 429 U1. This has a monolithic lens body with regulating elements arranged on its circumference, which are directly connected with the ciliary muscle of the eye. For accommodation, the lens body is moved by the ciliary muscle to and fro within the eye via the regulating elements.

Implantable monolithic lenses that can be adjusted by the ciliary muscle via the regulating elements have also been described in German Patent Nos. 201 11 320 U1 and No. 100 62 218 A1. In this case, the regulating elements are elastic elevators, which define an initial rest position of the lens when not in operation.

German Patent No. 101 39 027 describes an intraocular lens with preferably four haptics that radiate outward and are flexibly connected to the optical system. When the ciliary muscle contracts, the lens is supposed to be displaced forward axially in the light path with the aid of the guide mechanism, thereby increasing the refractivity of the entire system.

Such implants have so far produced an axial displacement of the lens by at most 300-500 mm, restoring an accommodation of 1-2 dioptres. The distance of objects at which the image on the retina is still in focus is then about 50-70 cm in the case of persons with normal sight (emmetropic subjects). However, this is not sufficient, because an accommodation of more than 3 dioptres is needed for near vision, e.g. for reading. For this, the axial displacement produced under the influence of the ciliary muscle would have to be at least 2 mm, which is not possible for anatomical reasons. See H. Schneider, O. Stachs and R. Guthoff, Evidenzbasierte Betrachtungen zu akkommodativen Kunstlinsen [=Evidence-based considerations about accommodative artificial lenses], lecture delivered at the 102nd Annual Meeting of the German Opthalmological Society, held in Berlin on 23-26 Sep. 2004. See also J. Kammann and G. Dornbach, Empirical results regarding accommodative lenses, In: Current Aspects of Human Accommodation, ed. by R. Guthoff and K. Ludwig, published by Kaden Verlag, Heidelberg, 2001, see pages 163-170.

Further International Patent WO 02/083033 describes a lens in the case of which the contraction of the ciliary muscle is supposed to displace a number of lens segments over one another via the deformation of the capsular sack, whereas German Patent No. 101 25 829 A1 describes a lens in which the radii of curvature of a sheath filled with a transparent material are supposed to change under the influence of the ciliary muscle on the capsular sack. However, clinical tests have disclosed that the accommodative effects of these methods are still inferior to the adjustment range that could be realized by displacement of the lens.

There are quite a few other propositions, that seek to solve the problem by applying adjustable technical optics, as U.S. Pat. No. 6,638,304, WO 2004/004,605 and WO 2004/004,605.

Similar devices for the restoration of the accommodative capacity are also known from German Patent No. 101 55 345 C2, U.S. Pat. No. 6,638,304 B2, International Patent WO 03/017 873 A1, U.S. Pat. No. 4,372,18, and lately in U.S. Pat. No. 8,043,370.

However, these solutions rely on accommodation with technical apparatus, the implantation of which into the human eye may be seen questionable.

Furthermore it is obvious, that systems of this complexity, having the need of particular sensors, electronic analysis, software and regulator control elements is not only hardly affordable to patients, but requires much space, comprising a yet unassigned power source of adequate capacity, that it seems hardly feasible at this state of the art to be realized as an eye implant.

Some advantage in more conventional systems is realized, if the haptics are of spiral shape, with some contact along to the rim of the lens, as shown in the earlier application DE 2004 029 384 A1. Other helical haptics, as in US 878.501.61.8/EP 0246 216 B1 to Bisonette or DE 41 100 16 869 C1 to Binder are also state of the art.

However, so far no design has managed to arrange the haptics in a way, that it would be safe and easy to insert the IOL, as well as effective in transmitting the constrictive momentum of the ciliary muscle.

Inventive Step

The inventive stop to solve these problems is, to realize an adaptive force, that would first keep the haptics densely clinging around the rim of the lens, but to deploy it in a way, that the haptics are inserted into the rim of the capsule sack with a force pushing the lens forward, when it contracts. This force is realized by application of memory material to the haptics, which contracts when cooled and expands at body temperature.

This had already been tried in Soviet patents, re-issued e.g. under DE3722732 A 1, with poor results, because the haptics were just radially orientated and had a small angle of enlacement.

The crucial innovation here is, that the haptics in cold state are pressed to the side of the rim of the IOL for optimal compact shape during operation, while in deployed state they fit into the ridge of the capsule sack. Furthermore, their ending in Slubs allow for a better contact to the rim of said capsule sack and prevent the quite stiff haptics from piercing it. Moreover, the latter inherit a certain twist, so to stabilize the capsule sack and better protrude the lens, if the spiral is contracted.

SUMMARY OF THE INVENTION

For to realize sufficient accommodation the two principles—protrusion and changing the curvature of the lens—are combined to apply the multiplicative impact of both together to allow for a wide 20 range of accommodation.

This is mated with haptics, that are flatly contracted at insertion, but expand inside of the eye, thus to provide good transmission of the contraction of the capsule sack or ciliar sulcus.

This is further provided by haptics made of change memory materials, such as polymeric or tissue-compatibly coated titan alloys, which in cold state—as provided—are formed so that the haptics cling to the rim of the lens, but when adapting to body temperature extend unto the rim of the capsule sack.

In a preferred embodiment these haptics are mounted on half-crescent adaptors to the lens for to provide equal pressure to it and avoid irregular deformation. In a further embodiment these haptics are circumfering the lens between 280° and 360° to enhance pressure distribution and—when unfolded—they inherit a slight twist backwards, so to make a perfect fit within the rim of the capsule sack. Furthermore the endpieces of said haptics are equipped with a slub, that fits into the capsule sack 35 with enlarged contact surface.

DESCRIPTION OF THE DRAWINGS

The here disclosed invention is more closely described by the following drawings.

Figure 1:
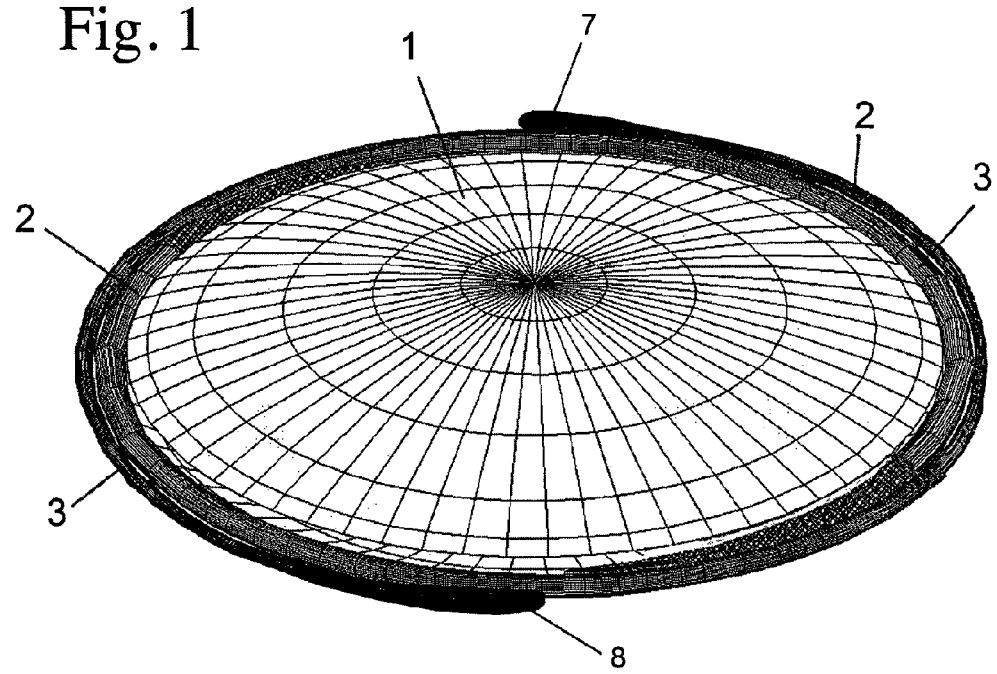
FIG. 1 shows the intra ocular lens 1 with circumferring haptics 2 and 3 and slubs 7 and 8 in their cold, contracted state, clinging to the edge of the lens 1.
Figure 3:
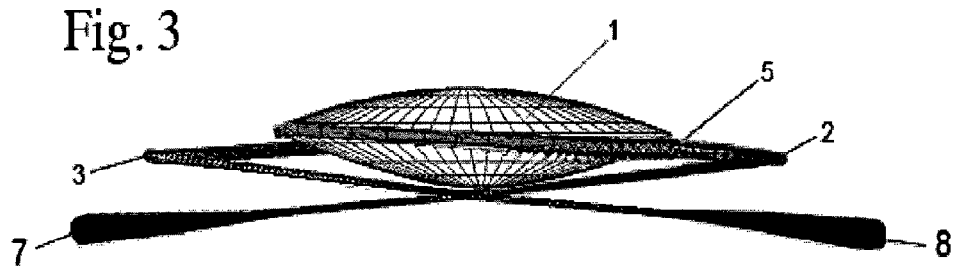
FIG. 3 demonstrates how the expanded haptics 2 and 3 with their slubs 7 and 8 are fixed to the supporting arches 4 (not seen) and 5 with a slight back offset, so protrude the lens, (here in already constricted shape) when the haptics are embraced with a tightening capsule sack.
Figure 2:
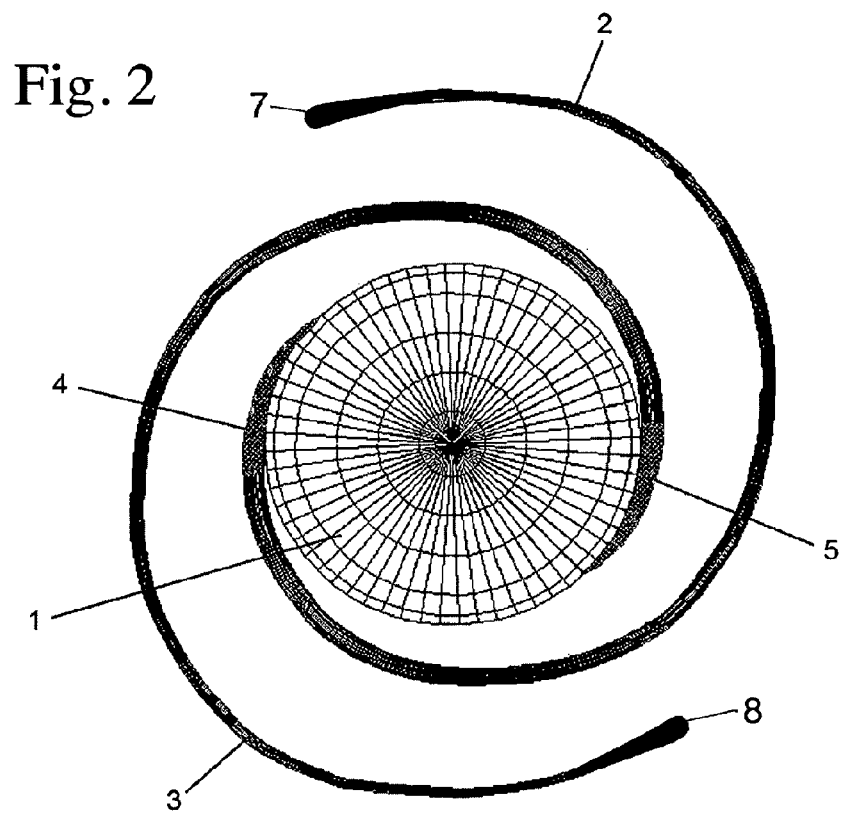
FIG. 2 shows in top view the same elements lens 1, and haptics 2 and 3 with slubs 7 and 8, now in expanded state, fastened to their half-crescent supporting arch 4 and 5, that connects them to the edge of the lens 1
Figure 4:
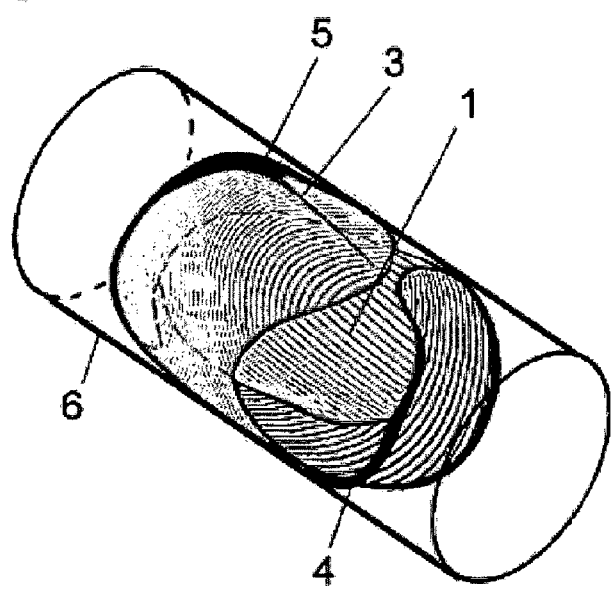
FIG. 4 shows the lens 1 with its haptics 2 (not visible) and 3, as well as its supporting half-cresents 4 and 5 as folded into a cannulae 6 for injection.

What is claimed is:

1. An artificial accommodative intraocular lens (IOL) for insertion into the capsular bag of a recipient's eye, the IOL consisting of
    a foldable optic comprising an anterior surface, a posterior surface, and a peripheral rim therebetween; and
    a pair of diametrically opposed helical haptics attached to said peripheral rim via half-crescent bracings and extending therefrom, wherein the helical haptics are made from a shape memory material,
    wherein in a cold state, the haptics encircle around the peripheral rim of the optic and are closely pressed against said peripheral rim, wherein in said cold state the haptics are positioned in the same plane as the optic,
    wherein at body temperature each of the haptics expands into a helical shape extending posteriorly from the optic, wherein each of the haptics circumfers around the optic from a half-crescent bracing unto a free end along an angle of from 280° up to 360°,
    wherein in the expanded condition, the haptics are as sufficiently stiff as to transmit pressure of a constricted capsule bag via said half-crescent bracing to the peripheral rim of the optic, thereby effectuating a change of the optic surface's curvature,
    wherein the central plain of the expanded haptics is tilted at 3° to 5° backwards, so as to bias the optic anteriorly when the capsule bag is constricted, and
    wherein the multiplicative effect of biasing and changing the curvature of the optic by compressing the peripheral rim of the optic is applied for close vision, and
    wherein the intraocular lens is folded into a cannulae for injection into a recipient's eye, and wherein the intraocular lens and the cannulae are pre-cooled to from +6 up to +8° Celsius before insertion of the intraocular lens.

2. The intraocular lens of claim 1, wherein the haptics consist of memory shape polymers.

3. The intraocular lens of claim 1, wherein the haptics consist of memory shape Titan alloys, coated with tissue-friendly material.

4. The intraocular lens of claim 1, wherein peaks of the expanded haptics are set to a maximum distance of 0.3 mm to the next haptic, thus limiting the biasing of the optic for not touching the iris.

5. The intraocular lens of claim 1, wherein the half-crescent bracings between haptics and the peripheral rim of the optic evenly distribute the pressure on the intraocular lens.

6. The intraocular lens of claim 1, comprising a slub at the free ends of the haptics, wherein the slubs are adapted to fit into an inner edge of the capsule bag.

\* \* \* \* \*